(12) United States Patent
Egelberg

(10) Patent No.: US 6,316,772 B1
(45) Date of Patent: Nov. 13, 2001

(54) DETERMINATION OF CONCENTRATION

(75) Inventor: Peter Egelberg, Lund (SE)

(73) Assignee: Agrovision AB, Lund (SE)

( * ) Notice: Subject to any disclaimer, the term of this patent is extended or adjusted under 35 U.S.C. 154(b) by 0 days.

(21) Appl. No.: 09/313,203

(22) Filed: May 18, 1999

(30) Foreign Application Priority Data

May 19, 1998 (SE) .................................................. 9801776

(51) Int. Cl.[7] .................................................. G01N 21/35
(52) U.S. Cl. .............................. 250/339.11; 250/339.12; 250/339.02
(58) Field of Search .................... 250/339.11, 339.12, 250/343, 358.1, 359.1, 330, 339.02, 339.01, 338.5

(56) References Cited

U.S. PATENT DOCUMENTS

| | | |
|---|---|---|
| 5,321,265 | 6/1994 | Block . |
| 5,351,303 | 9/1994 | Willmore . |
| 5,504,332 | 4/1996 | Richmond et al. . |
| 5,603,413 * | 2/1997 | Mitchum, Jr. ........................ 209/580 |
| 5,606,413 * | 2/1997 | Bellus et al. ........................ 356/326 |
| 5,646,405 * | 7/1997 | Nevel et al. ........................ 250/341.6 |
| 5,745,243 * | 4/1998 | Wilcox et al. ........................ 356/419 |
| 5,900,634 * | 5/1999 | Soloman ........................ 250/339.11 |
| 6,020,588 * | 1/2000 | Ditmarsen et al. ............ 250/339.12 |

FOREIGN PATENT DOCUMENTS

| | | |
|---|---|---|
| 0767369 | 4/1997 | (EP) . |
| 2292798 | 3/1996 | (GB) . |
| 9622511 | 7/1996 | (WO) . |
| 9624835 | 8/1996 | (WO) . |

OTHER PUBLICATIONS

Baronti, S., et al., "Principal Component Analysis of Visible and Near–Infrared Multispectral Images of Works of Art," *Chemometrics and Intelligent Laboratory Systems*39, 1997, pp. 103–114.

Taylor, S., et al., "NIR Imaging Spectroscopy: Measuring the Distribution of Chemical Components," North Carolina State University, pp. 393–403.

"Measurement of Oxygen and Carbon Concentrations In Silicon Wafers by Using Infrared Vidicon Camera," *IBM Technical Disclosure Bulletin*, vol. 28, No. 3, Aug. 1985, pp. 1180–1181.

* cited by examiner

Primary Examiner—Constantine Hannaher
Assistant Examiner—Albert Gagliardi

(57) ABSTRACT

An apparatus for determining the concentration of a first component in a mixture of at least two components, which have different absorption properties in the IR range, comprises image recording means which are adapted to image the mixture by means of IR radiation to produce at least one image. The apparatus further comprises image processing means which, with the aid of intensity values for pixels in the image which represent the mixture, determine the concentration of the first component in the mixture.

22 Claims, 2 Drawing Sheets

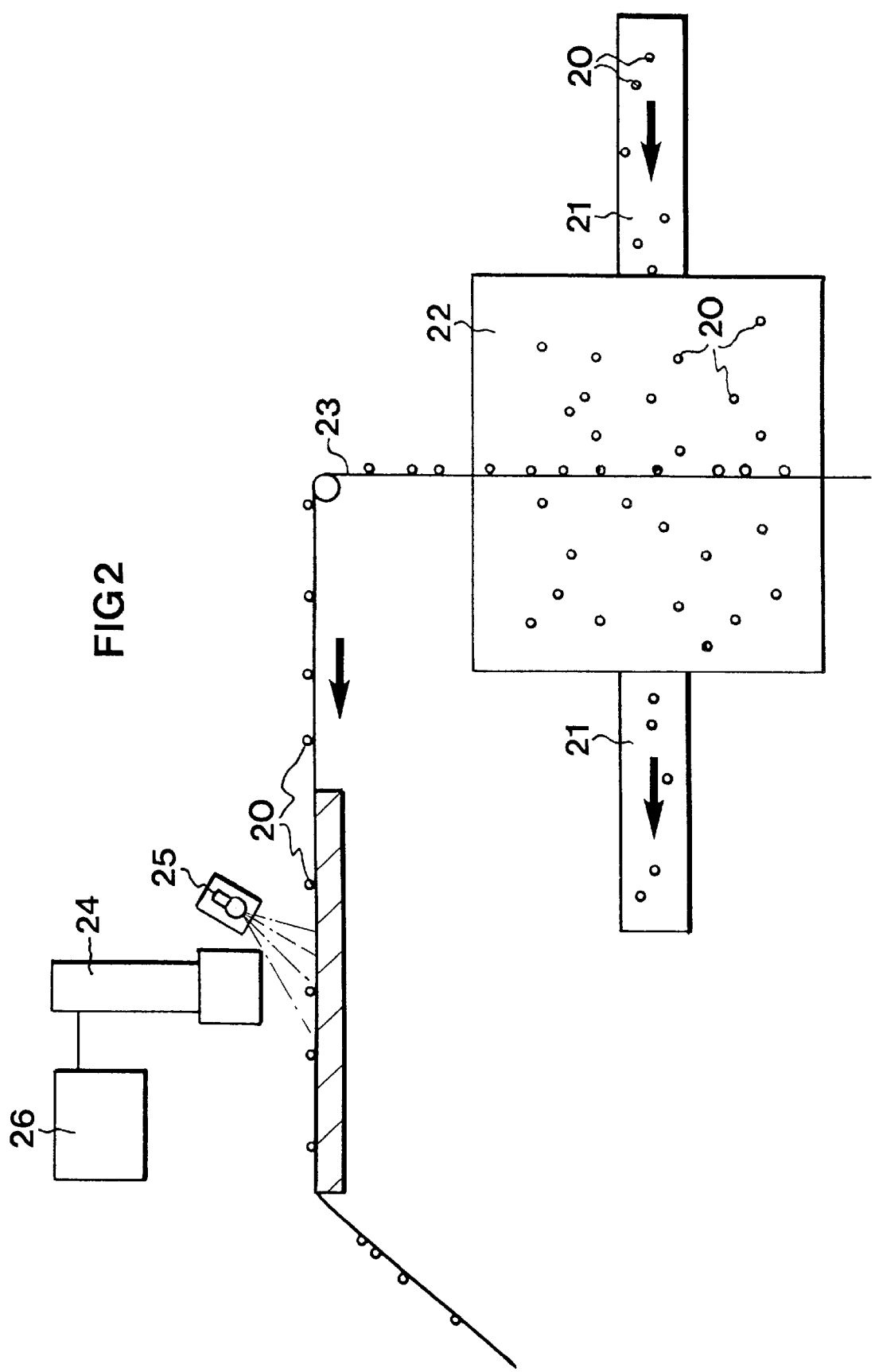

DETERMINATION OF CONCENTRATION

FIELD OF THE INVENTION

The present invention relates to an apparatus for determining the concentration of a first component in a mixture of at least two components which have different absorption properties in the IR range.

BACKGROUND ART

In the manufacture of pharmaceutical preparations, an active substance is in many cases mixed with an inactive substance to achieve a sufficient volume of the pharmaceutical preparation and to obtain suitable properties of the pharmaceutical preparation. The substances frequently have the form of powder consisting of a variety of particles. Moreover, it is normally large volumes of powder that are mixed to manufacture a large number of doses of the pharmaceutical preparation. It is then most important for the mixture to be homogeneous so that the concentration of the active substance is the same in all doses, for instance in all tablets, that are manufactured from the mixture.

There is today a tendency towards the active substance being more and more potent, and consequently a smaller and smaller volume of active substance need be added to the inactive substance in mixing. This makes it more difficult to provide a homogeneous mixture. It is also difficult to preserve the homogeneity in the mixtures since pulverulent mixtures tend to form layers.

A further difficulty associated with the homogeneity arises in the manufacture of divisible tablets. Some tablets are formed with a notch indicating that these tablets may be divided to allow the user to take half a dose of the pharmaceutical preparation. For such tablets, the manufacturer must be able to guarantee that the concentration of the active substance is the desired one not only in the tablet in its entirety but also in each half of the tablet.

The homogeneity in a powder mixture can be monitored by sampling the mixture at different points of time. If the concentration of the active substance is the desired in each sample, it is assumed that the mixture is homogeneous and that the concentration in all manufactured doses is correct. Correspondingly, when manufacturing tablets, random sampling of tablets from the manufacturing line is made and the concentration is determined. If the concentration is correct, it is assumed that all tablets have the correct concentration. The concentration of the active substance in powders and tablets is in many cases determined by a wet-chemical or dry-chemical method.

An alternative method of determining the homogeneity in tablets is disclosed in U.S. Pat. No. 5,504,332. According to this patent, a NIR reflection spectrum for a pharmaceutical tablet is generated, the homogeneity of which is to be determined. This spectrum is then compared with an index (recognition index) which has been determined on the basis of spectra of previously analyzed, acceptable tablets to determine whether the homogeneity of the tablet in question is acceptable.

A drawback of this method is that it is slow since it is necessary to generate an entire spectrum for each tablet. Further it is not possible to determine how the active substance is distributed in the tablet. Nor can the method be used to study particles of the size that exists in powders.

Also in other fields in industry, there is a need to monitor the homogeneity in mixtures by measuring the concentration of a component in the mixture.

SUMMARY OF THE INVENTION

An object of the present invention therefore is to provide an improved apparatus for determining the concentration of a first component in a mixture of at least two components.

This object is achieved by an apparatus which has the features defined in claim 1. Preferred embodiments of the apparatus are recited in the subclaims depended from claim 1.

More specifically, the invention concerns an apparatus of the type described by way of introduction and characterized by image recording means which are adapted to image the mixture by means of IR radiation to produce at least one image, on the basis of which it is possible to determine the concentration of said first component in the mixture.

This apparatus thus is based on the idea that it is possible to use images and image analysis instead of spectrum and spectrum analysis to determine the concentration in a mixture. This is advantageous since it is a much quicker and much easier operation to record an image than to generate a spectrum which requires that the light be spectrally divided. This results, in turn, in the possibility of analyzing all tablets in the manufacture, which yields a much greater safety than random sampling.

An image further contains position information. The image of the mixture can thus supply information on how the components and, in particular, the active component are distributed in the mixture.

The image recording means can be any means whatever that are sensitive to IR radiation and that render it possible to produce a two-dimensional "IR image". They may comprise, for instance, a line sensor which produces an image by scanning. They can record one or more images of the mixture, for instance, images that are based on IR radiation at different wavelengths.

The image recording means can be adapted to carry out the imaging by means of IR radiation that is reflected from the mixture or transmitted through the mixture. Sometimes a combination of these alternatives can be advantageous.

The advantage of using reflected radiation is that the position information will be improved so that it will be possible to determine, for instance, the distribution of the interesting component in a tablet or the like where the particles in the mixture are compressed into a unit. The drawback is that the reflected radiation supplies information merely on the particles to a certain level of penetration. IR radiation transmitted through a mixture supplies information on particles at all levels in the mixture. On the other hand, this IR radiation supplies poorer position information since the transmitted light is scattered by the particles on which it falls.

With a view to obtaining clear distinctions between the two components, it is convenient to record the image of the mixture by means of radiation at one or more wavelengths where there is a great difference between the absorption properties of the components. To this end, the image recording means advantageously comprise a filter for selecting at least one wavelength at which the components have different absorption properties. The selection of a suitable wavelength/suitable wavelengths is made individually for each specific substance that is to be monitored. In this manner, a monochromatic image of the mixture is produced.

Alternatively, the image recording means may comprise at least two filters for performing the imaging by means of IR radiation from two different wavelengths ranges to produce an image of the mixture in "IR color" in a manner corresponding to that in which ordinary color images with red, green and blue light are produced.

The IR radiation is advantageously NIR radiation since biologically active substances included in, inter alia, pharmaceutical preparations in most cases have characteristic absorption properties in the NIR range.

An electronic image is composed of a large number of pixels each having one or more intensity values. In an IR image, each pixel has at least one IR intensity value which yields a measure of the intensity of the IR radiation which has fallen on a corresponding point on a sensor in the image recording means. Knowing the absorption properties of the components contained in the imaged mixture in respect of the IR wavelengths involved, it is then possible to determine which pixels represent the different components and, thus, the concentration thereof. The apparatus therefore suitably comprises image processing means which are adapted to determine, with the aid of intensity values for pixels in the image of the mixture, the concentration of said first component in the mixture. The image processing means can advantageously consist of a suitably programmed computer. If the image of the mixtures is monochromatic, the computer can determine, for instance, the concentration of the interesting component by using threshold values for the intensity values. If the image is in "IR color", the "IR color" can instead be used for determining the concentration.

The apparatus is advantageously also adapted to determine, on the basis of the image of the mixture, the distribution of the first component in the mixture. This can also be carried out by means of a suitably programmed computer.

The apparatus can be used to determine the concentration of a component in a number of different mixtures. The mixture may consist of, for instance, a plurality of particles which are suspended in a liquid or gas. The mixture may also consist of a single particle containing different substances. It may also consist of droplets of a first component in an emulsion.

In an advantageous embodiment, the apparatus is used to determine the concentration of the first component in a mixture which is present in the form of an ointment on a carrier, such as an adhesive plaster. It is becoming more and more common to dose pharmaceutical preparations as an ointment on an adhesive plaster. Up to now, it has only been possible to analyze the concentration of the active substance in random samples of the ointment before applying it to the adhesive plaster, but the invention makes it possible to easily determine both the concentration and the distribution of the active substance on each piece of adhesive plaster. This is advantageous since the later in the manufacturing process the quality control can be performed the greater reliability is achieved. Moreover, it is possible to determine, on the basis of the image of the adhesive plaster with the ointment, the distribution of the ointment on the adhesive plaster, its thickness and other parameters of interest.

In an advantageous embodiment, the apparatus can be used to determine the concentration of the first component in the mixture when the mixture is in the form of separate particles, e.g. particles that exist freely from each other, such as in a powder. The particles can be analyzed on a carrier in the form of an adhesive plaster, a piece of adhesive tape or something else to which the particles can adhere, or when they are spread on an arbitrary base. This embodiment can be of interest during manufacture before the mixture has been tabletted or to control a completed pharmaceutical preparation when being supplied to the patient by means of an adhesive plaster. To this end, the apparatus suitably comprises image processing means which are adapted to identify in said image pixels representing each of the particles and, on the basis of the intensity of the pixels, determine to which of the components each particle belongs. Each particle can be imaged by means of one or more pixels, and by determining whether the intensity values of these pixels correspond to the radiation that can be expected from the one component or the other, it is thus possible to determine whether the particle belongs to the one component or the other. By the image processing means then counting, for instance, how many particles or pixels belong to the one component or the other, the concentration of the first component can be determined.

In a further advantageous embodiment, the apparatus is used to determine the concentration of the first component in the mixture when the mixture is present in the form of a tablet. Tablet is here to be interpreted in a wide sense and comprises, for example, granules, pellets, capsules, sugar-coated pills and all other dosing forms in which a variety of particles are joined to a unit. The tablet can be analyzed as it is or when packed in an IR-transparent container.

To allow the concentration of the first component to be determined in a tablet, the apparatus suitably comprises image processing means, which are adapted to identify in said picture pixels representing the tablet and, on the basis of the intensity of the pixels, determine the concentration of the first component in the tablet. By studying the position in the image of pixels which represent the first component, it is also possible to determine the distribution thereof in the tablet.

In an advantageous embodiment, the image processing means are adapted to determine whether the tablet has a desired composition, which may relate to the concentration of the first component as well as the distribution thereof. The apparatus then comprises a separating mechanism, which is adapted to discard, under the action of the image processing means, the tablet if it is not composed as desired. In this manner, a fully automated quality control is obtained, which ensures that only such tablets as satisfy the quality requirements are made to advance in the manufacture.

In many of the applications where one wants to determine the concentration of a first component in a mixture, it is also interesting to determine other parameters, such as size and shape. Therefore the apparatus is advantageously adapted to determine a size parameter and/or a shape parameter for the mixture. The apparatus may comprise special software for this purpose. The size parameter can be, for instance, the size of a particle or a tablet, or the distribution of the mixture on a carrier. The shape parameter can be, for instance, the form of a tablet or a particle. With the aid of the size and shape parameters it is then possible to determine the volume and mass by correlation.

The apparatus is particularly suited for concentration determination when the first component is a biologically active substance, preferably a pharmacologically active substance.

In a second aspect of the invention, it concerns an apparatus for determining the homogeneity, that is the distribution, of a first component in a mixture of at least two components, which have different absorption properties in the IR range, the image recording means being adapted to image the mixture by means of IR radiation to produce at least one image, on the basis of which it is possible to determine the homogeneity or distribution of said first component in the mixture. The advantages of this aspect of the apparatus are evident from that stated above.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will now be described by way of an embodiment with reference to the accompanying drawings, in which FIG. 2 is a schematic view of a second example of how an apparatus according to the invention can be accomplished.

DESCRIPTION OF A PREFERRED EMBODIMENT

Figure 1:
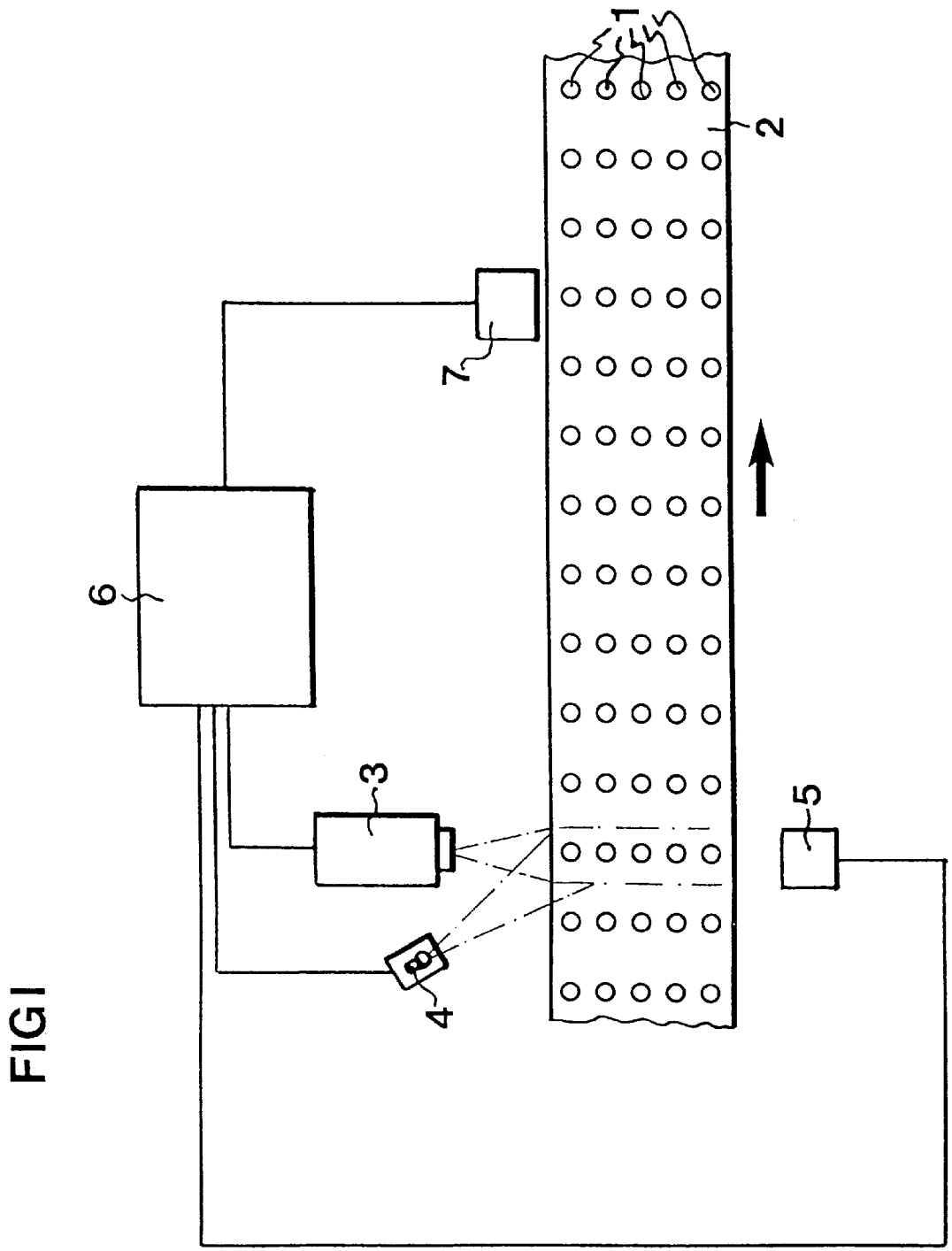
FIG. 1 is a schematic view of a first example of how an apparatus according to the invention can be accomplished.

FIG. 1 shows an apparatus for determining the concentration of a biologically active substance in pharmaceutical tablets containing a mixture of the active substance and an inactive substance. In this example, the tablets 1 are arranged in rows of five tablets on a travelling belt 2. The apparatus comprises an image recording means in the form of a NIR camera 3, a lighting fitting 4, a triggering unit 5, a computer 6 and a separating mechanism 7.

The NIR camera 3 consists of a CCD camera which is provided with a NIR filter which lets through NIR radiation having a desired wavelength. The NIR camera takes an image of each row of tablets 1 passing through its lens coverage. In this example, the camera records the NIR radiation reflected from the tablets. If transmitted radiation is to be recorded, the camera must be placed in such manner that it can receive radiation that has passed through the tablets.

The lighting fitting 4 is a broadband lamp having a strong emission in the NIR range.

The triggering unit 5 is a sensor which detects when a new row of tablets passes in front of it and emits a signal to the NIR camera 3 through the computer 6 instructing the NIR camera to take an image.

The separating mechanism 7 consists of a movable arm which, by applying subatmospheric pressure, lifts and discards tablets 1 which the computer 6 has assessed not to have the desired composition.

The computer 6, which is connected to the NIR camera 3, the lighting fitting 4, the triggering unit 5 and the separating mechanism 7, comprises software for the accomplishing of image processing means.

The apparatus operates as follows. The tablets 1 on the belt 2 are illuminated with NIR radiation from the lighting fitting 4. When the triggering unit 5 detects that a new row of tablets 1 is passing in the front of it, it triggers the camera 3 to take an image of the tablets in this row. The image is transferred to the computer 6, which identifies which pixels in the image correspond to the tablets. This can be carried out, for instance, with the aid of threshold values which separate the tablets from the background. Subsequently, the computer determines with the aid of the intensity values of the pixels which pixels in each tablet correspond to the biologically active substance and which correspond to the inactive substance. This is also carried out with the aid of threshold values. After that, the computer can determine both the concentration of the active substance in the tablet and the distribution thereof.

The concentration and distribution for each of the tablets in the image are compared with predetermined quality requirements. If a tablet does not satisfy the quality requirements, the computer signals to the separating mechanism 7 that the defective tablet is to be discarded, which occurs when the tablet in question passes the separating mechanism.

FIG. 2 illustrates how an apparatus according to the invention can be composed if the concentration of a biologically active substance is to be determined in a mixture which is present in the form of a powder, from which random samples are to be taken. The powder, which consists of a very large number of particles 20, is transported in a duct 21. The duct contains a cyclone chamber 22 in which the particles are made to eddy in air. Through the cyclone chamber, a plastic adhesive tape 23 is passed, to which certain particles adhere. The plastic adhesive tape 23 is made to pass in front of a camera 24 while being illuminated with NIR light from a lamp 25. The camera takes images at such a frequency that each particle is to be seen in an image. The images are then processed in a computer 26, which is connected to the camera 24 and determines which particles belong to which component. By counting the number of particles of each component, the computer can determine whether the mixture has the desired concentration. In this embodiment, neither triggering means nor separating mechanism is required. The concentration is determined in reflected light, but can, of course, just as well be determined in transmitted light. The apparatus can be used, for instance, to control a tablet manufacturing process so that the tablets are made of the powder only when the powder has the correct composition.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What I claim and desire to secure by Letters Patent is:

1. An apparatus for determining the concentration of a first component in a mixture of at least two components, which have different absorption properties in the IR range and which are present in the form of separate particles, comprising:

image recording means for imaging the mixture by means of IR radiation to produce at least one image, on the basis of which it is possible to determine the concentration of said first component in the mixture; and image processing means for identifying in said image, pixels representing each of the particles and, on the basis of the intensity of the pixels, for determining to which of the components each particle belongs, wherein said image processing means further includes means for determining a size parameter and/or a shape parameter for the particles.

2. The apparatus as claimed in claim 1, wherein the image recording means are adapted to perform the imaging by means of IR radiation reflected from the mixture.

3. The apparatus as claimed in claim 1, wherein the image recording means are adapted to perform the imaging by means of IR radiation transmitted through the mixture.

4. The apparatus as claimed in claim 1, wherein the image recording means comprise a filter for selecting at least one wavelength in the IR range, at which the at least two components have different absorption properties.

5. The apparatus as claimed in claim 1, wherein the image recording means comprise at least two filters for performing the imaging by means of IR radiation from at least two wavelength ranges.

6. The apparatus as claimed in claim 1, wherein the IR radiation includes NIR radiation.

7. The apparatus as claimed in claim 1, wherein said image processing means includes means for determining, with the aid of intensity values for pixels in the image of the mixture, the concentration of said first component in the mixture.

8. The apparatus as claimed in claim 1, wherein the apparatus includes means for determining, on the basis of the image of the mixture, the distribution of the first component in the mixture.

9. An apparatus for determining the concentration of a first component in a mixture of at least two components, which have different absorption properties in the IR range and which are present in the form of a tablet including a large number of particles which have been pressed together, comprising:

image recording means for imaging the mixture by means of IR radiation to produce at least one image, on the basis of which it is possible to determine the concentration of said first component in the mixture; and image processing means for identifying in said image, pixels representing the tablet and, on the basis of the intensity of the pixels, for determining the concentration of the first component in the tablet, wherein the image processing means includes means for determining the distribution of the first component in the tablet.

10. The apparatus as claimed in claim 9, wherein the image processing means includes means for determining if the tablet has the desired composition, the apparatus further comprising a separating mechanism for discarding, under the action of the image processing means, the tablet if it does not have the desired composition.

11. The apparatus as claimed in claim 9, wherein the image recording means are adapted to perform the imaging by means of IR radiation reflected from the mixture.

12. The apparatus as claimed in claim 9, wherein the image recording means are adapted to perform the imaging by means of IR radiation transmitted through the mixture.

13. The apparatus as claimed in claim 9, wherein the image recording means comprise a filter for selecting at least one wavelength in the IR range, at which the at least two components have different absorption properties.

14. The apparatus as claimed in claim 9, wherein the image recording means comprise at least two filters for performing the imaging by means of IR radiation from at least two wavelength ranges.

15. The apparatus as claimed in claim 9, wherein the IR radiation includes NIR radiation.

16. The apparatus as claimed in claim 9, wherein said image processing means further comprises means for determining, with the aid of intensity values for pixels in the image of the mixture, the concentration of said first component in the mixture.

17. The apparatus as claimed in claim 9, wherein the apparatus includes means for determining a size parameter and/or a shape parameter for the mixture.

18. The apparatus as claimed in claim 9, wherein the first component is a pharmacologically active substance.

19. The apparatus as claimed in claim 1, wherein the first component is a pharmacologically active substance.

20. The apparatus as claimed in claim 9, wherein the mixture is present in the form of a plurality of tablets and the image recording means includes an IR camera, through the lens coverage of which the tablets are moved, the apparatus further comprising an illuminating means for illuminating the tablets with IR radiation, means for triggering the IR camera to image each tablet, image processing means for determining the concentration of the first component in each tablet on the basis of the intensity values in the images and further for determining whether the concentration in each tablet satisfies a predetermined quality requirement, and a separating mechanism for discarding such tablets as do not satisfy said quality requirement.

21. An apparatus for determining the homogeneity of a first component in a mixture of at least two components, which have different absorption properties in the IR range, and which are present in the form of tablets, comprising:

image recording means for imaging the mixture by means of IR radiation to produce at least one image, on the basis of which it is possible to determine the homogeneity of said first component in the mixture; and image processing means for identifying in said picture, pixels representing the tablet and, on the basis of the intensity of the pixels, for determining the concentration of the first component in the tablet, wherein the image processing means includes means for determining the homogeneity of the first component in the tablet.

22. A method for determining the concentration of a first component in a mixture of at least two components, which have different absorption properties in the IR range and which are present in the form of separate particles, comprising the steps of:

imaging the mixture by means of IR radiation to produce at least one image, on the basis of which it is possible to determine the concentration of said first component in the mixture;

processing the image to identify in said image, pixels representing each of the particles and, on the basis of the intensity of the pixels, determining which of the components each particle belongs; and determining a size parameter and/or a shape parameter for the particles from the processed image.

* * * * *